United States Patent [19]

Joppien

[11] 4,103,007
[45] Jul. 25, 1978

[54] PESTICIDAL SYNERGISTIC MIXTURE OF A DIOXATHIEPIN AND A FORMAMIDINE

[75] Inventor: Hartmut Joppien, Berlin, Fed. Rep. of Germany

[73] Assignee: Schering Aktiengesellschaft, Berlin and Bergkamen, Fed. Rep. of Germany

[21] Appl. No.: 792,593

[22] Filed: May 2, 1977

[30] Foreign Application Priority Data

May 5, 1976 [DE] Fed. Rep. of Germany ....... 2619834

[51] Int. Cl.² .......................... A01N 9/12; A01N 9/28
[52] U.S. Cl. ...................................... 424/244; 424/326
[58] Field of Search ................................ 424/244, 326

[56] References Cited

U.S. PATENT DOCUMENTS

| 3,496,270 | 2/1970 | Counselman | 424/244 |
| 3,629,460 | 12/1971 | Dittrich | 424/326 |

OTHER PUBLICATIONS

Chemical Abstracts, vol. 53 (1959), p. 16023h.

Primary Examiner—V. D. Turner
Attorney, Agent, or Firm—Michael J. Striker

[57] ABSTRACT

A pesticide which is composed of a mixture of a dioxathiepin derivative of the formula

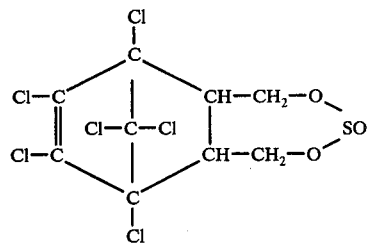

with at least one formamidine derivative of the formula

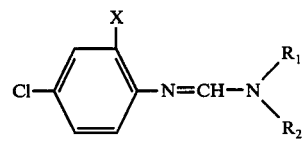

in which $R_1$ is hydrogen or methyl, $R_2$ is alkyl of 1 to 4 carbon atoms and X is hydrogen or methyl, or salts thereof. The mixture has a substantially higher activity against plant and animal parasites than the activity sum of the individual components. The invention embraces also a pesticide composition in which a compound as set out is at least one of the active ingredients and which in addition includes a liquid or solid carrier material.

14 Claims, No Drawings

PESTICIDAL SYNERGISTIC MIXTURE OF A DIOXATHIEPIN AND A FORMAMIDINE

BACKGROUND OF THE INVENTION

The insecticidal properties of 6,7,8,9,10,10-hexachloro-1,5,5a,6,9,9a-hexahydro-6,9-methano-2,4,3-benzodioxathiepin-3-oxide are already known (see German Pat. No. 1,015,797). It is also known that formamidine derivatives have an acaricidal and insecticidal effect (see German Patent 1,172,081 and Swiss Pat. No. 533,423).

SUMMARY OF THE INVENTION

It has now been found that a mixture of a compound of the formula

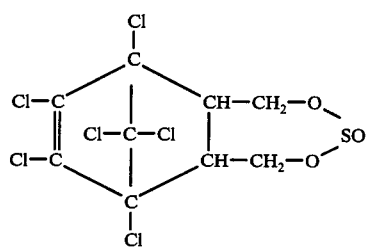

which corresponds to the compound: 6,7,8,9,10,10-hexachloro-1,5,5a,6,9,9a-hexahydro-6,9-methano-2,4,3-benzo-dioxathiepin-3-oxide with at least one formamidine of the formula

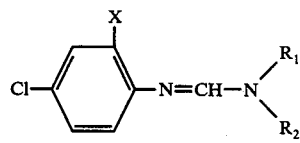

in which $R_1$ is hydrogen or methyl, $R_2$ is alkyl of 1-4 carbon atoms and X is hydrogen or methyl, or a salt thereof, has a substantially greater effect against plant and animal parasites than the sum of the activity of the individual components when used alone. The present invention therefore relates to this type of mixture and also to pesticide compositions in which this mixture constitutes one of the active ingredients.

This enhancement of the activity of the individual components in the mixture of the invention is surprising and could not be predicted since predictions along this line are simply not possible because of the absence of any knowledge about the function on which these mechanisms are based.

A particular advantage of the mixture is that in order to obtain the same amount of activity against many different pests, smaller amounts of active agent may be used than with use of the individual components. The pests can therefore be destroyed with a greater chance of success, with less risk and in a more economical way. Furthermore, the necessary time interval between the last treatment of the culture and harvest can be substantially reduced. Among the pests that can be effectively kept down by means of the mixture of the invention there may be mentioned the following: *Musca domestica* (housefly), grain pests like *Sitophilus granarius* or *Calandra granaria Tenebrio molitor* (black mealworm), and a cotton pest like *Spondoptera littoralis*. It is noted that the effect with these tests is present in all stages of the development of the insects.

A further advantage of the compounds of the invention is that the individual components of the mixture are not harmful to bees, and if they are properly employed have no inherent problems due to persistence, either by a too extended permanence per se or by accumulation (storing) properties in the environment.

DISCUSSION OF THE INVENTION AND OF SPECIAL EMBODIMENTS

As individual components for the mixture of the invention the following are of particular significance. All these individual components, however, it is noted, are known per se and can be made by known processes.

The mixture accordingly preferably is constituted as follows:

A. Formamidine derivatives of the following constitution:

N-(2-methyl-4-chlorophenyl)-N'-methyl-formamidine

N-(2-methyl-4-chlorophenyl)-N',N'-dimethyl-formamidine

N-(2-methyl-4-chlorophenyl)-N'-methyl-N'-n-butyl-formamidine

N-(2-methyl-4-chlorophenyl)-N'-methyl-N'-isobutyl-formamidine

N-(2-methyl-4-chlorophenyl)-N'-methyl-N'-sec.-butyl-formamidine

N-(2-methyl-4-chlorophenyl)-N'-methyl-N'-propyl-formamidine

N-(4-chlorophenyl)-N',N'-dimethyl-formamidine

N-(4-chlorophenyl)-N'-methyl-formamidine

These formamidine derivatives may be used as such or in the form of their salts with inorganic or organic acids, for instance hydrochlorides.

B. 6,7,8,9,10,10-hexachloro-1,5,5a,6,9,9a-hexahydro-6,9-methano-2,4,3-benzo-dioxathiepin-3-oxide of the formula

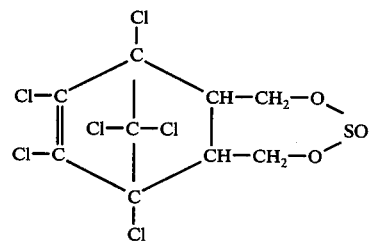

The mixtures of the invention can be used as such or together with other pesticides such as insecticides, acaricides or fungicides. The mixtures can be set up in the usual form as conventional in plant protection compositions by employing liquid or solid carrier materials.

Suitable liquid carriers are among others, water, mineral oils or solvents. Suitable solid carriers are for instance, bentonite, fuller's earth, gypsum, lime, kieselguhr, pyrophyllite, silicon dioxide or talc.

The compositions may also include additives such as emulsifiers, cross-linking or binding agents, propelling gases, perfuming agents, stabilizers, bait agents, or insect repellents.

The compositions can be applied in the form of dust, sprays or granulates, in particular as liquids which may be applied by atomizing, spraying or befogging, or in the form of aerosols or fumigants, The amount of the mixture according to the invention which can be used in pesticides and plant protection agents, for instance in insecticides or acaricides can be varied in a wide range. It depends among others on the ratio of components, on the type of preparation, on the type of application, on the desired destructive effects and on the type of pests to be destroyed.

Depending on the form of the preparation the contents of active mixture in the compositions may be between 0.1 and 90% by weight. The individual components can be used in concentrations going down to 0.001% by weight.

In general, concentrations between 0.01 and 1.0% active agent in liquid or solid carriers have resulted in excellent effects. For some purposes higher concentrations may be used up to about 25% by weight.

In the mixtures of the invention the weight ratio of the formamidine derivatives A to the component B may vary in general between 1 : 100 and 200 : 1. Particularly good results have been obtained with a weight ratio of formamidine derivative A to component B between 1 : 10 and 100 : 1.

The mixtures of the invention can be prepared in conventional form by mixing or grinding processes.

The following Examples will further illustrate the invention. Reference is made to Table 1 which follows: In this table the designations used have the following meaning:

A I = N-(2-methyl-4-chlorophenyl)-N'-methyl-formamidine

A II = N-(2-methyl-4-chlorophenyl)-N'-N'-dimethyl-formamidine

A III = N-(2-methyl-4-chlorophenyl)-N'-methyl-N'-n-butyl-formamidine

A IV = N-(2-methyl-4-chlorophenyl)-N'-methyl-N'-iso-butyl-formamidine

A V = N-(2-methyl-4-chlorophenyl)-N'-methyl-N'-sec.-butyl-formamidine

A VI = N-(2-methyl-4-chlorophenyl)-N'-methyl-N'-propyl-formamidine

A VII = N-(4-chlorophenyl)-N',N'-dimethyl-formamidine

A VIII = N-(4-chlorophenyl)-N'-methyl-formamidine

B = 6,7,8,9,10,11-hexachloro-1,5,5a,6,9,9a-hexahydro-6,9-methano-2,4,3-benzo-dioxathiepin-3-oxide The cotoxicity coefficients which are used in these examples indicate the strength of the synergistic action. They have been calculated according to the formulas found in Sun und Johnson, Journ, Econ. Entomol., vol. 53, no. 5, pp. 887–892, 1960.

Accordingly, the cotoxicity coefficient for additive effect is 100, while any cotoxicity coefficient which is larger than 100 indicates a synergistic effect.

EXAMPLE 1

Again referring to the following Table 1 the table includes the $LC_{50}$ values of the mixtures of the invention and of the individual components. In addition there are shown the cotoxicity coefficients for the mixtures calculated as just indicated.

The figures were obtained with aqueous emulsions of the individual components and of the mixtures in the concentrations indicated.

These emulsions were then sprayed on glass slides in a dosage of 4 mg/cm$^2$.

25 adult houseflies (*Musca domestica*) were then exposed to the deposits formed on the glass slides after drying and likewise to receptacles containing sugar water for 24 hours in glass cylinders.

The criterion for the activity was the mortality of the flies in percentages after 24 hours. On this basis the $LC_{50}$ values and the cotoxicity coefficients were figured as conventional.

TABLE I

| Compound | Weight ratio | $LC_{50}$ in % | Cotoxicity coefficient |
|---|---|---|---|
| A II |  | 0.45 |  |
| B |  | 0.0014 |  |
| A II + B | 200 : 1 | 0.065 | 266 |
| A II + B | 100 : 1 | 0.048 | 224 |
| A II + B | 10 : 1 | 0.009 | 165 |

Analogous effects were shown by mixtures of the components A I, A III, A IV, A V, A VI, A VII and A VIII with the component B.

EXAMPLE 2

The following Table 2 shows the $LC_{50}$ values of the mixtures of the invention and of the individual components. For the mixtures there are, in addition, listed the cotoxicity coefficients calculated as above stated in Sun and Johnson.

The figures were again obtained by using aqueous emulsions of the individual components and of the mixtures in the concentrations indicated. These emulsions were then applied to the bottoms of glass petri dishes in a dosage of 4 mg/cm$^2$ by spraying. After the deposits had dried 100 adult grain pests of the type (*Sitophilus granarius*) were exposed to the compounds and compositions for 4 days in the dark.

The standard for the assaying of the activity was the mortality of the bugs in percentages after 4 days. On this basis the $LC_{50}$ values and the cotoxicity coefficients were calculated as usual:

TABLE 2

| Compound | Weight ratio | $LC_{50}$ in % | Cotoxicity coefficient |
|---|---|---|---|
| A II |  | 0.65 |  |
| B |  | 0.0025 |  |
| A II + B | 200 : 1 | 0.15 | 189 |
| A II + B | 100 : 1 | 0.09 | 203 |
| A II + B | 1 : 1 | 0.0039 | 123 |

EXAMPLE 3

In the following Table 3 the $LC_{50}$ values of the mixtures of the invention and of the individual components are shown. For the mixtures there are also listed in each case the cotoxicity coefficients calculated as above stated. The determinations were again made by using aqueous emulsions of the individual components and their mixtures in the concentrations indicated.

In each case 2 ml of the spray composition of varying concentration were applied to 50 cc of a mixture of sand and earth in petri dishes of a plastic material. To this substrate there were then exposed in each case 10 juvenile larvae of the black mealworm (*Tenebrio molitor*) for 7 days.

The standard for judging the activity was the mortality of the larvae in percentages after 7 days. On this basis the $LC_{50}$ value and the cotoxicity coefficient was figured as usual:

TABLE 3

| Compound | Weight ratio | $LC_{50}$ in % | Cotoxicity coefficient |
|---|---|---|---|
| A II |  | 3.4 |  |
| B |  | 0.012 |  |
| A II + B | 100 : 1 | 0.23 | 389 |

EXAMPLE 4

The following Table 4 shows the $LC_{50}$ values for mixtures of the invention and their individual components. In addition there are again shown the cotoxicity coefficient for the mixtures calculated as above indicated. To establish the figures there were again used aqueous emulsions of the individual components and of the mixtures in the concentrations given. With these emulsions 1 day old eggs were sprayed with an amount of 4 mg/cm². The eggs were laid by female spider mites of the type (Tetranychus urticae) on bushbean leaf pieces. The treated leaves were then kept for 7 days in the laboratory until the hatching out of the mites without any further treatment or handling.

The standard for judging the activity was the mortality of the eggs and of the juvenile larvae in percentages after 7 days. On this basis the $LC_{50}$ and the cotoxicity coefficients were figured as usual.

TABLE 4

| Compound | Weight ratio | $LC_{50}$ in % | Cotoxicity coefficient |
|---|---|---|---|
| A II | | 0.0008 | |
| B | | 0.12 | |
| A II + B | 1 : 1 | 0.0008 | 198 |
| A II + B | 1 : 5 | 0.0025 | 185 |

EXAMPLE 5

In connection with the following Table 5 aqueous emulsions were again used of the individual components and of the mixtures in the concentrations indicated. With these emulsions bushbean plants were sprayed of the type (Phaseolus vulgaris) until dripping wet. The bushbean plants had been placed in pots and had been infested with chlorodimeform-resistant spider mites of the type (Tetranychus urticae). The plants were then placed in a hothouse for 14 days. Thereafter the suction damage to the pinnate leaves was determined in percentages. The suction damage of the untreated plants was put at 100%. The figures were then converted to activity percentages. By means of these activity percentages the $WC_{50}$ values were graphically determined. These were the concentrations at which the suction damage was reduced by 50% as compared with the untreated plots. Following the method of Sun and Johnson, but modifying it, there were then calculated the coactivity coefficients instead of the cotoxicity coefficients previously used.

TABLE 5

| Compound | Weight ratio | $WC_{50}$ in % | Coactivity coefficient |
|---|---|---|---|
| A II | | 0.023 | |
| B | | 0.037 | |
| A II + B | 1 : 1 | 0.0038 | 746 |
| A II + B | 1 : 5 | 0.0035 | 958 |

EXAMPLE 6

In this example in connection with following Table 6 there were again used aqueous emulsions of the individual components and of their mixtures at the concentrations indicated.

With these emulsions potted bushbean plants of the type Phaseolus vulgaris were sprayed until they were dripping wet. The plants had been infested with spider mites of normal sensitivity belonging to the type Tetranychus urticae. The plants were then kept for 14 days in a hothouse.

Thereafter the suction damage to the pinnate leaves was estimated in percentages. The suction damage in the untreated plants was again set at 100%. There were thus calculated the activity percentages. By means of the latter percentages the $WC_{50}$ values were again graphically determined, that is, the concentrations at which the suction damage was reduced by 50% compared with the untreated plants. Following, but modifying the method of Sun and Johnson there were then calculated the coactivity coefficients instead of the cotoxicity coefficients used in Examples 1 to 4.

TABLE 6

| Compound | Weight ratio | $WC_{50}$ in % | Coactivity coefficient |
|---|---|---|---|
| A II | | 0.0086 | |
| B | | 0.066 | |
| A II + B | 1 : 1 | 0.0062 | 246 |
| A II + B | 1 : 5 | 0.013 | 240 |
| A I | | 0.0052 | |
| A I + B | 1 : 1 | 0.0043 | 224 |
| A I + B | 1 : 5 | 0.011 | 289 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A pesticide of high insecticidal and acaricidal activity comprising, as active ingredients, a mixture of
   A. a formamidine derivative of the formula

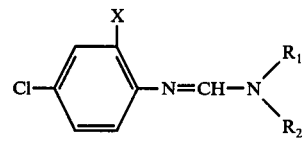

in which $R_1$ is hydrogen or methyl $R_2$ is alkyl of 1 to 4 carbon atoms and X is hydrogen or methyl, or a salt thereof having insecticidal and acaricidal activity
with
   B. A dioxathiepin of the formula

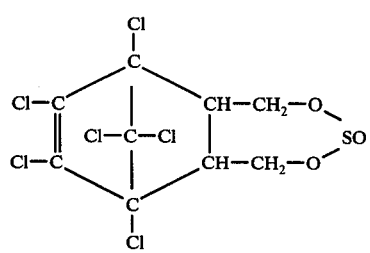

the ratio of compounds A and B being between about 200 : 1 and 1 : 5.

2. The pesticide of claim 1 wherein the formamidine salt is the hydrochloride.

3. The pesticide of claim 1 wherein the formamidine derivative is N-(2-methyl-4-chlorophenyl)-N'-methylformamidine.

4. The pesticide of claim 1 wherein the formamidine derivative is N-(2-methyl-4-chlorophenyl)-N',N'-dimethyl-formamidine.

5. The pesticide of claim 1 wherein the formamidine derivative is N-(2-methyl-4-chlorophenyl)-N'-methyl-N'-n-butyl-formamidine.

6. The pesticide of claim 1 wherein the formamidine derivative is N-(2-methyl-4-chlorophenyl)-N'-methyl-N'-iso-butyl-formamidine.

7. The pesticide of claim 1 wherein the formamidine derivative is N-(2-methyl-4-chlorophenyl)-N'-methyl-N'-sec.-butyl-formamidine.

8. The pesticide of claim 1 wherein the formamidine derivative is N-(2-methyl-4-chlorophenyl)-N'-methyl-N'-propyl-formamidine.

9. The pesticide of claim 1 wherein the formamidine derivative is N-(4-chlorophenyl)-N',N'-dimethyl-formamidine.

10. The pesticide of claim 1 wherein the formamidine derivative is N-(4-chlorophenyl)-N'-methyl-formamidine.

11. The pesticide of claim 1 wherein the ratio of component A to component B is between 1 : 5 and 200 : 1 by weight.

12. The pesticide of claim 11 wherein the ratio of component A to component B is between 1 : 5 and 100 : 1.

13. A pesticide composition including the mixture of claim 1 together with a liquid or solid carrier material therefor.

14. The pesticide composition of claim 13 wherein the total mixture of active ingredients is present in an amount of 0.1 to 90% by weight.

* * * * *